US008009352B2

(12) United States Patent
Soon

(10) Patent No.: US 8,009,352 B2
(45) Date of Patent: Aug. 30, 2011

(54) MICROSCOPE WITH CENTERED ILLUMINATION

(75) Inventor: Haw Chong Soon, Widnau (CH)

(73) Assignee: Leica Instruments (Singapore) Pte. Ltd, Singapore (SG)

( * ) Notice: Subject to any disclaimer, the term of this patent is extended or adjusted under 35 U.S.C. 154(b) by 476 days.

(21) Appl. No.: 12/145,839

(22) Filed: Jun. 25, 2008

(65) Prior Publication Data

US 2009/0002813 A1 Jan. 1, 2009

(30) Foreign Application Priority Data

Jun. 28, 2007 (DE) .................. 10 2007 029 894

(51) Int. Cl.
*G02B 21/06* (2006.01)
(52) U.S. Cl. ........................ 359/388
(58) Field of Classification Search .......... 359/385, 359/388, 389
See application file for complete search history.

(56) References Cited

U.S. PATENT DOCUMENTS

| 5,748,367 | A  | * | 5/1998  | Lucke et al. ............ | 359/385 |
| 6,473,229 | B2 |   | 10/2002 | Nakamura |  |
| 7,057,807 | B2 | * | 6/2006  | Sander ................ | 359/380 |
| 7,102,818 | B2 |   | 9/2006  | Sander |  |
| 2001/0010592 | A1 |   | 8/2001  | Nakamura |  |
| 2003/0048530 | A1 |   | 3/2003  | Sander |  |
| 2004/0057108 | A1 |   | 3/2004  | Namii |  |
| 2007/0285770 | A1 | * | 12/2007 | Sander ................ | 359/385 |
| 2009/0002812 | A1 | * | 1/2009  | Kuster ................ | 359/385 |

FOREIGN PATENT DOCUMENTS

| DE | 195 23 712 C2 | 1/1996 |
| DE | 195 37 868 B4 | 4/1996 |
| DE | 10144062 | 3/2003 |
| EP | 0 321 586 B2 | 6/1989 |
| EP | 1 424 582 B1 | 6/2004 |
| EP | 1424582 | 6/2004 |

OTHER PUBLICATIONS

Office Action issued by the United States Patent and Trademark Office for U.S. Appl. No. 12/145,868 dated Jun. 8, 2009.
Office Action issued by the United States Patent and Trademark Office for U.S. Appl. No. 12/145,868 dated Mar. 31, 2010.
Office Action issued by the United States Patent and Trademark Office for U.S. Appl. No. 12/145,863 dated Jan. 12, 2010.
Office Action issued by the United States Patent and Trademark Office for U.S. Appl. No. 12/145,863 dated Mar. 18, 2010.
Office Action issued by the United States Patent and Trademark Office for U.S. Appl. No. 12/145,863 dated Apr. 21, 2010.
Office Action issued by the United States Patent and Trademark Office for U.S. Appl. No. 12/145,863 dated Jun. 12, 2009.
Office Action issued by the United States Patent and Trademark Office for U.S. Appl. No. 12/145,868 dated Dec. 3, 2010.

(Continued)

*Primary Examiner* — Alessandro Amari
(74) *Attorney, Agent, or Firm* — Schlee IP International, P.C.; Alexander R. Schlee

(57) ABSTRACT

A microscope comprising a main objective having a variable focal length and comprising an illuminating unit including a light source and an illuminating optical system for generating an illuminating beam path directed onto the object plane and extending outside the main objective. A unit is provided for centering the illumination dependent on a variation of the focal length of the main objective. The illuminating optical system is mounted at least in part in a laterally shiftable manner for centering the illumination.

26 Claims, 3 Drawing Sheets

OTHER PUBLICATIONS

Notice of Allowance issued by the United States Patent and Trademark Office for U.S. Appl. No. 12/145,863 dated Jan. 21, 2011.

Office Action issued by the United States Patent and Trademark Office for U.S. Appl. No, 12/145,863 dated Oct. 13, 2010.

* cited by examiner

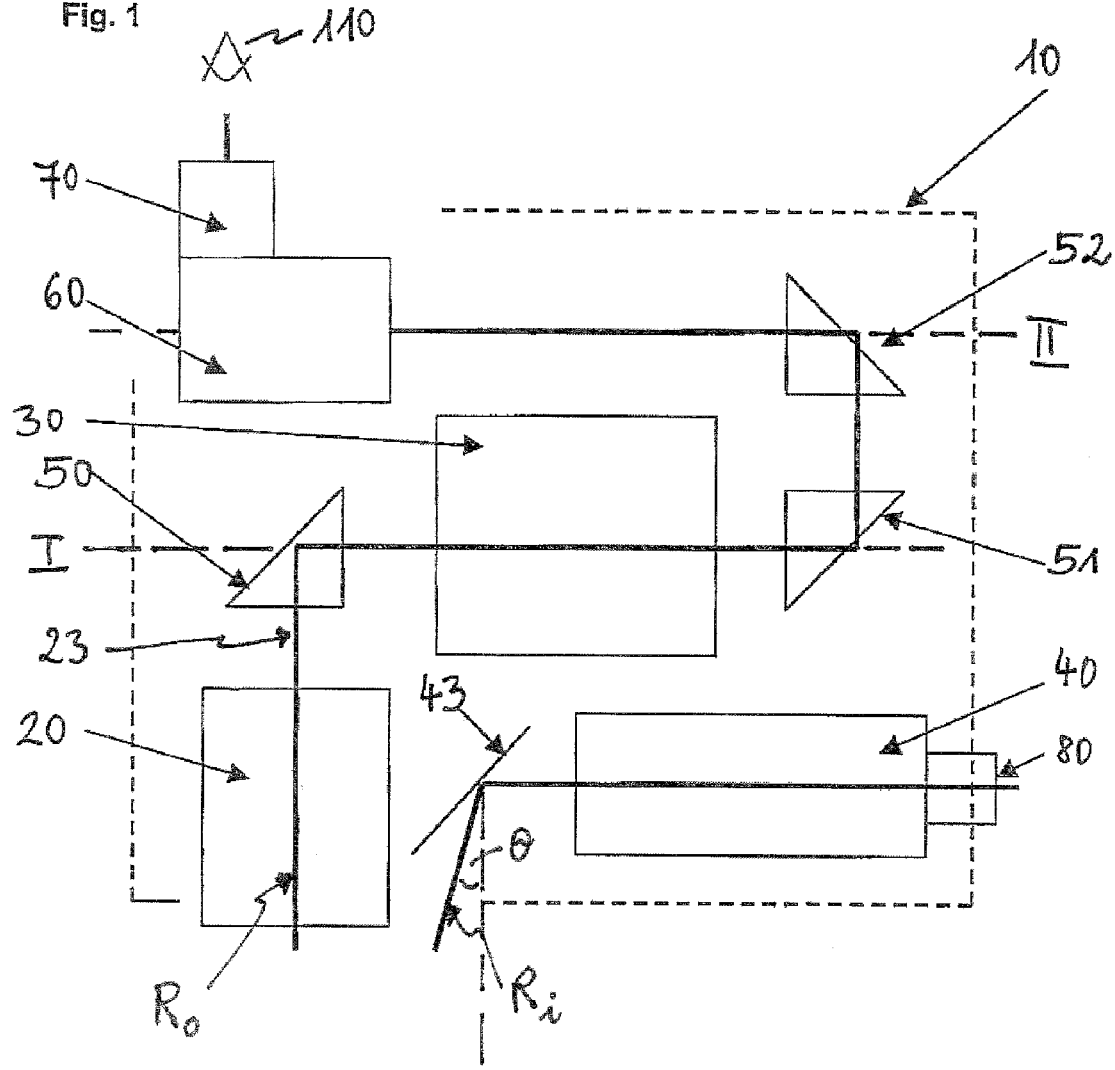
Fig. 1

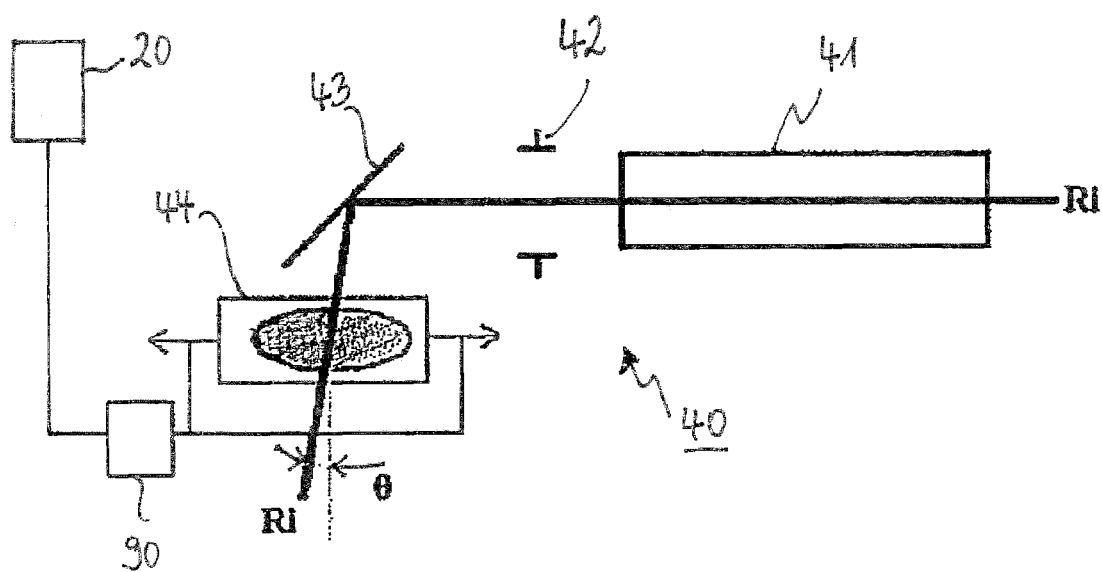
Fig. 3
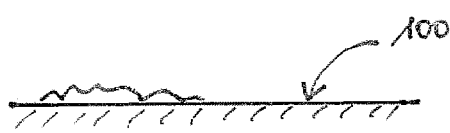

MICROSCOPE WITH CENTERED ILLUMINATION

This application claims the priority of the German patent application DE 10 2007 029 894.5 having a filing date of Jun. 28, 2007, the entire content of which is herewith incorporated by reference.

BACKGROUND OF THE INVENTION

The present invention relates to a microscope comprising a main objective having a variable focal length and comprising an illuminating unit including a light source and an illuminating optical system for generating an illuminating beam path directed onto an object plane and extending outside the main objective, means being provided for centering the illumination dependent on a variation of the focal length of the main objective.

Microscopes of this type are known from DE 195 23 712 C2 and DE 195 37 868 B4. In the first-mentioned DE 195 23 712 C2 a stereomicroscope comprising a main objective with variable focal length, a downstream zoom system and a binocular tube as well as an illuminating unit arranged adjacent to the main objective is disclosed. The main objective comprises a fixed and a movable lens for varying the focal length and the intercept length of the main objective. The fixed, negative lens of the main objective is arranged towards the object plane, the movable, positive lens is arranged behind it (facing away from the object plane). A movement of the movable lens in the direction away from the object plane results in a reduction of the focal length of the main objective. For an optimal illumination of the vertically shifting object plane, it is suggested in this document to adjust the position of an illumination deflector element dependent on a focal length variation of the main objective for centering the illumination. This is done in that the prism lens used as an illumination deflector element is pivoted such that the illuminating beam path tracks the shifted object plane. For this purpose, the prism lens is pivotally mounted about an axis which is perpendicular to a plane that is spanned by the vertical optical axis of the main objective and the illuminating beam path which is incident substantially horizontally inclined on the prism lens. As a result thereof, for all positions of the movable lens of the main objective facing away from the object a focusing of the illuminating light on the respective focal point of the main objective can be guaranteed.

The coupling of the rotary movement of the illumination deflector element with the linear (vertical) movement of the lens of the main objective facing away from the object, as suggested in this document, requires very sensitive rotary movements of the illumination deflector element in relation to the movement of the lens and makes high demands on the mechanical coupling which is designed with a high constructional expense in this document. Any disturbances will be directly visible for the user (particularly given high magnifications). Further, the size of the surface of the deflector element turns out to be disadvantageous, as it has to be sufficiently large in order to cover the entire illuminating pencil even when the illumination deflector element is tilted. Mirrors or the mentioned prism lenses can be used as illumination deflector elements. When mirrors are used, an enlargement of the reflecting surface will result in the additional disadvantage of an increased required thickness of the reflecting surface. Thus, altogether the required space and the height of the weight to be moved are increased.

In the mentioned DE 195 37 868 B4, an illuminating device for a stereomicroscope comprising an objective with a variable image-forming intercept length is disclosed, an illumination intercept length variation being possible via an optical system that is separate from the viewing optical system. Means for coupling the intercept lengths mentioned are disclosed, which means effect that the illumination intercept length and the image-forming intercept length correspond to one another. Further, means for coupling are provided which guarantee that the angular position of a deflector element of the illuminating device is varied such dependent on the respective image-forming intercept length and illumination intercept length that there is always a centered illumination of the viewed field of view. Since, here too, for centering the illumination rotary movements of the illumination deflector element are performed, here, once again, the disadvantages mentioned occur.

A basically different possibility of illumination centering results when the illumination is guided through the main objective of the microscope. This solution is implemented in the surgical microscope models M520 and M525 of the applicant. Here, the illumination deflector element directs the illuminating beam path to and through the main objective having variable focal length so that the illumination is always centered on the focus.

An optical binocular viewing system comprising one main objective common for both channels and a viewing zoom system as well as an illuminating system having an illuminating zoom system is suggested in EP 0 321 586 B2. The illuminating beam path is guided through the main objective via a deflecting prism. The illuminating zoom system is adjusted dependent on the viewing zoom system in order to adapt the size of the illuminated field to the varying zoom magnification.

The microscopes mentioned up to now use vertical zoom systems, i.e. the longitudinal axis of the zoom system lies parallel to the optical axis of the main objective. If, in addition, the illumination is fed into the main objective from above, there will be a high space requirement in vertical direction resulting in microscopes having a relative high overall height in the vertical direction. This is disadvantageous for ergonomic reasons since the distance between the eyepiece and the main objective is increased.

From U.S. Pat. No. 6,473,229 B2, a stereomicroscope comprising a horizontally arranged illuminating unit is known, the illuminating beam path of which being directed via a fixed deflecting mirror outside the main objective onto the object plane. The stereomicroscope suggested therein has a main beam path and an assistant beam path, for each of the two beam paths separate optical systems comprising a lens system, a zoom system and a binocular tube being provided. While one of the zoom systems is designed such that it lies horizontally, the axis of the other zoom system is inclined to the vertical which is perpendicular to the object plane. Here, with respect to illumination centering given a variable focal length of one of the lens systems no suggestions are made.

For reducing the vertical constructional height, a stereomicroscope structure has been suggested in EP 1 424 582 B1, in which a "lying" zoom system, i.e. a zoom system having its longitudinal axis arranged horizontally, is realized. For this purpose, there is arranged between the main objective and the zoom system a deflector element which deflects the viewing beam path from a substantially vertical direction into a substantially horizontal direction and feeds the same to the zoom system arranged in a first horizontal plane. By means of further deflector elements the viewing beam path exiting the zoom system is deflected into a second horizontal plane which extends substantially parallel to the first horizontal plane and in which optical add-on components are arranged.

With respect to details on the structure and the mode of functioning of such a stereomicroscope with "lying" zoom system reference is explicitly made to the mentioned European patent specification.

In this stereomicroscope, the illuminating unit is arranged substantially adjacent to the main objective in horizontal direction und below the zoom system in vertical direction, the illuminating beam path being guided outside the main objective. Instead of an illumination centering, it can be ensured by means of a sufficiently large illuminated field that the visual field is always illuminated given a focal length variation of the main objective. Such a generously designed illuminated field requires a correspondingly largely designed illuminating aperture and thus illuminating unit which in turn has a negative effect on the ergonomics of the microscope. A further disadvantage is here that the homogeneity of the illumination (distribution of the illuminated field) is not formed for all positions of the multi-focus (variable focus lens). By using a variable focus lens different object planes can be focused in a certain area.

The inventive microscope further comprises an illuminating unit including a light source and an illuminating optical system for generating an illuminating beam path directed onto an object plane and extending outside the main objective.

SUMMARY OF THE INVENTION

According to the invention, the illuminating optical system is mounted at least partially laterally shiftably for centering the illumination dependent on a variation in focal length of the main objective. The term "laterally shiftably" means in this connection a shiftability not only in axial direction, i.e. not exclusively in the direction of the illuminating axis, but in a direction inclined thereto or perpendicular thereto, whereby an additional shifting component in axial direction shall not be excluded. It turned out that by means of such a lateral shifting of at least a part of the illuminating optical system, the illuminating focus can technically easily and reliably be tracked to the focus of the main objective. Thus by a lateral shifting of the illuminating field said illuminating field tracks the field of view. Further, it turned out that it is sufficient to design only part of the illuminating optical system laterally shiftably. This is advantageous since in this way not the entire illuminating unit has to be mounted shiftably but only a part of the actual illuminating optical system. In addition, a tracking of the illuminated field with respect to position and size has the advantage that the diameter of the illuminated field can be kept at a minimum and be adapted to the field of view so that in the case of surgical microscopes the patient will be exposed to a minimum of radiation.

An illuminating unit used for the invention advantageously has, as seen from the light source, as an illuminating optical system a collector, a diaphragm as well as an illuminating lens assembly for focusing the illuminating beam path into the object plane. The opening of the diaphragm, often an iris diaphragm having a variable diameter, is imaged via the lens assembly on the object plane given Köhler illumination. Other types of illumination as well as illumination units structured otherwise can be used. An illumination deflector element can be arranged downstream or preferably upstream of the illumination lens assembly. As a result thereof, it is in particular possible to use an illuminating unit (for example light source, collector and diaphragm) arranged at least partially horizontally and to deflect the generated illuminating beam path by means of the illumination deflector element in a vertical direction in the direction of the object plane.

It turned out that in particular in case of this kind of structure of an illuminating unit, it is sufficiently according to the invention to mount only the mentioned lens assembly or a part thereof laterally shiftably. The illumination lens assembly itself can in principle represent a single lens or a combination of lenses. Instead of the lateral shiftability of the entire lens assembly it can be sufficient in the last case, if only one or specific lenses of the combination of lenses are laterally shifted to achieve the desired centering of the illumination.

As mentioned, the illuminating unit is often at least partially arranged such that the generated illuminating beam path is incident on the illumination deflector element in a direction that is substantially perpendicular (or inclined) to the optical axis of the main objective, which, without restricting the generality, is substantially vertically directed ("horizontal illuminating unit"). The illumination deflector element deflects this illuminating beam path then in the direction of the object plane on the focus of the main objective. This section of the deflected illuminating beam path encloses a specific angle with the vertical (normal to the object plane). Given a variation of the focal length of the main objective which results in a shifting of the imaged object plane in vertical direction given this arrangement, this angle likewise has to be varied so that the illumination remains centered. Surprisingly, it turned out that this variation of said angle can simply be done by a lateral shifting of the illumination lens group (in particular of the illumination lens group downstream of the deflector element). In particular, a linear shifting of the illumination lens assembly is sufficient and this shifting can take place preferably parallel to the object plane in the case of a lens assembly arranged downstream of the deflector element.

With respect to the orientation of the lens assembly two advantageous embodiments shall be mentioned: Firstly the symmetrical axis of the lens assembly can be aligned parallel to the axis of the illuminating beam path. The lateral shifting can for example again take place parallel to the object plane in the case of the above-mentioned microscope illumination arrangement. As a consequence the lens assembly is then tiltably arranged with respect to the lateral direction of movement. In the case of a circular lens and diaphragm geometry, the illuminating field generated on a horizontal object plane in this case has an elliptic geometry, as the axis of the illuminating beam path is not perpendicular to the object plane. As a consequence, the orientation of the lens assembly can be utilized systematically to influence the geometry of the illuminating field. For example, the symmetrical axis of the lens assembly can be aligned perpendicular to the object plane in another case and remain aligned in this way during the lateral shifting. In principle it would also be conceivable to change the orientation of the lens assembly during a lateral shifting, for example in order to make corrections of the illuminating field geometry.

In principle, also other lateral shiftings are conceivable, for example such shiftings, which are perpendicular on the illuminating axis coming from the illumination deflector element or shiftings along a curved path, thus, for example along a circular path of a circle with the center in the illumination deflector element. However, the mentioned lateral shifting parallel to the object plane proved to be realizable in a particular easy and technically reliable manner in case of the structure of the illuminating unit described here.

It is expedient if a control unit for coupling a variation of the focal length of the main objective with an amount of lateral shift of the at least one part of the illuminating optical system is provided. Here, it is useful, with respect to the specific microscope structure comprising the specific illuminating unit, to assign at least for a number of working distances (or, respectively, focal lengths of the main objective) the correspondingly necessary lateral shift amounts and to derive a corresponding relationship therefrom (numerical or in the form of a formula), which is afterwards entered into a corresponding control. The mentioned relationship can also be established with the aid of suitable software by ray tracing given different working distances and a best-fit method. A closed loop control of the illumination centering can also be considered.

It is noted that the features of the invention which have already been mentioned and which are still to be mentioned cannot be used only in the combination given herein but, as far as technically useful, also alone or in other combinations, without leaving the scope of the present invention.

In the following, an embodiment illustrated schematically in the drawing shall explain the invention and its advantages in more detail.

BRIEF DESCRIPTION OF THE DRAWINGS

FIG. 1 schematically shows the structure of a microscope with which the invention can preferably be used.

FIG. 3 schematically shows a cutout of the microscope according to FIG. 1, which only shows the essential components of the invention.

DETAILED DESCRIPTION OF THE DRAWINGS

Figure 2:
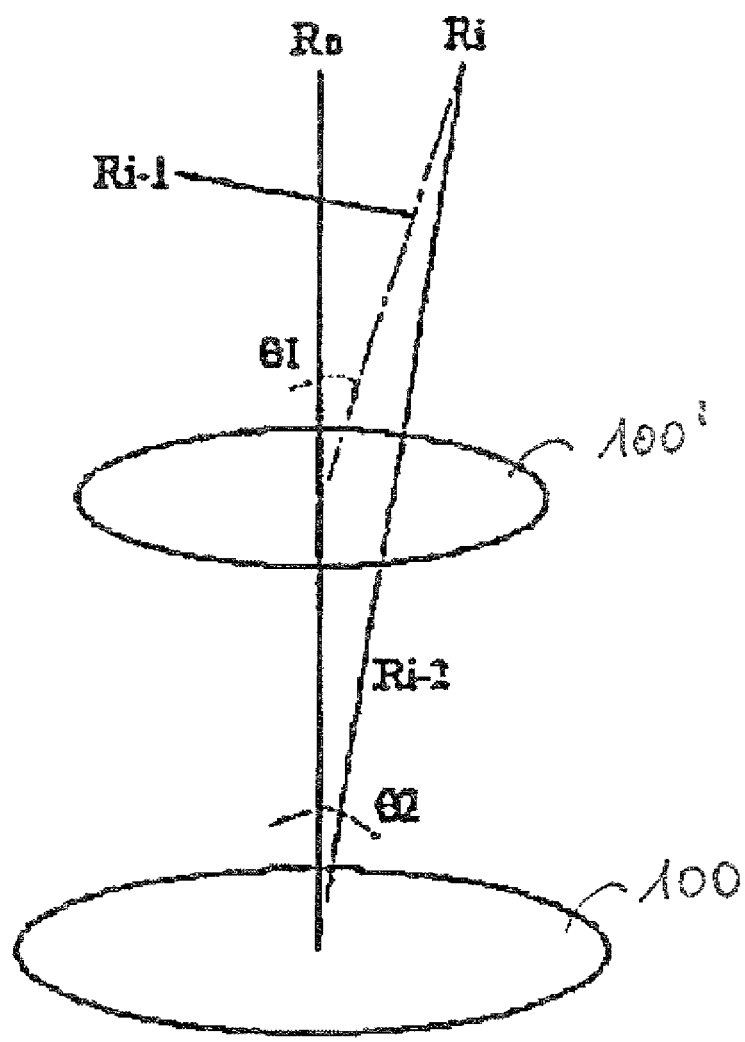
FIG. 2 shows the influence of a varied operating distance on the illumination centering.

FIG. 1 schematically shows the basic structure of a microscope 10, here designed as a surgical stereomicroscope, for a better illustration only the viewing axis $R_o$ being illustrated. Such surgical microscopes often have an additional pair of viewing beam paths for assistant's viewing in addition to a pair of main viewing beam paths. Microscopes of this type are known per se and therefore are not to be explained in more detail here. In this connection, reference is made to the stereomicroscope described in the already mentioned EP 1 424 582 B1 in which, as in the present case, a "lying" zoom system 30 is realized.

The surgical microscope 10 comprises a main objective 20 which is designed as a multi-focus (or variable focus lens), i.e. represents a lens having a variable focal length. The main objective 20 defines an optical axis 23 which is perpendicular to an object plane 100. By varying the focal length of the main objective 20, focusing on the respective object plane 100 can be effected. The viewing beam paths run parallel to the shown optical axis 23 and lie, for example, either in the drawing plane or in a plane perpendicular to the drawing plane and including the optical axis 23. For deflecting the viewing beam paths a first deflector element 50 is arranged in the beam path and deflects the viewing beam paths from a substantially vertical direction into a substantially horizontal direction into the "lying" zoom system 30. The zoom system 30 is arranged with its longitudinal axis in a first horizontal plane I. Instead of a zoom system 30 which serves for the continuous magnification of the object image a discretely operating magnification changer can likewise be provided. By means of further deflector elements 51 and 52, the viewing beam path is directed into a second horizontal plane II. Here, the tube 60 is arranged, which directs the illuminating beam path into at least one eyepiece 70 through which an observer 110 can view the microscope image. The principle structure of the described microscope components such as main objective, zoom system, tube and eyepiece or binocular tube is common knowledge for the person skilled in the art. In the beam path illustrated in FIG. 1, optical add-on components such as filters, image inverters, components for extending the optical path length, beam splitters for assistant's viewing and reflecting-in and reflecting-out devices (for example data reflecting-in devices) etc. can be arranged. Finally, between the zoom system 30 and the tube 60 an output (optical/mechanical) for documentation (camera, video, etc.) can be present.

An illuminating unit 40 which can be arranged ergonomically favorable with its longitudinal axis substantially horizontally below the zoom system 30 serves for the illumination of the object. What is illustrated here is a fiber illumination via a light guide 80. However, a direct halogen, xenon or LED illumination can likewise be used. The illuminating beam path generated by the illuminating unit 40 and illustrated by means of its illuminating axis $R_i$ is directed by means of an illumination deflector mirror 43 in the direction of the object plane 100. As can be taken from FIG. 1, the illuminating beam path is guided outside the main objective 20 of the microscope 10. Therefore, given a focal length variation of the main objective 20 resulting in a shifting of the object plane 100 in vertical direction, the illuminating beam path has to be tracked for an optimal illumination. The inventive type of this tracking of the illumination shall be explained in more detail on the basis of FIG. 3.

As can be taken from FIG. 1, the axis $R_i$ of the illuminating beam path encloses the angle θ with the axis $R_o$ of the viewing beam path.

FIG. 2 illustrates the required change of the mentioned angle θ given a focal length variation of the main objective 20 or given a variation in the working distance between this main objective 20 and the object plane 100. With decreasing focal length of the main objective 20 and thus decreasing working distance, the angle θ is increased. FIG. 2 shows two extreme positions, for example maximum and minimum working distance, the axis $R_{i2}$ of the illuminating beam path being directed onto the focus of the main objective 20 given a greater working distance. Here, the angle $θ_2$ results. Given a smaller working distance, the angle θ has to be increased, until, for example, the angle $θ_1$ with the associated illuminating axis $R_{i1}$ is reached. From the maximum and the minimum working distance of the main objective 20, thus a range for the angle θ can be given which is to be tracked given a change in the working distance in order to achieve a centered illumination.

FIG. 3 now shows the measures necessary therefor according to the invention in a specific embodiment. In FIG. 3, the structure of an illuminating unit 40 is illustrated, as it shall preferably be used for the present invention. The collector (here with the light source) is designated with 41. The collector collects the light from the light source and images the same via the diaphragm 42 and the illuminating lens assembly 44 into the object plane 100. The diaphragm 42 concerned is preferably an iris diaphragm with variable diameter. A plane mirror or also a spherical mirror can be used as an illumination deflector element 43. The illumination lens assembly 44 is preferably (as viewed from the light source) arranged downstream of the illumination deflector element 43. This is a difference to the illuminating unit 40, as it has been described in FIG. 1. The illuminating lens assembly 44 can represent a single lens or (as usual) a combination of lenses. In this embodiment the symmetrical axis of the lens assembly 44 is orientated perpendicular to the object plane 100. To simplify matters, the entire lens assembly 44 is illustrated laterally shiftably in FIG. 3. However, it shall be emphasized that it can be sufficient in case of a many-membered structure to design only individual parts of this lens assembly laterally shiftably. In particular, also individual parts of this lens assembly could be arranged upstream of the illumination deflector element 43, others could be arranged downstream of the illumination deflector element 43.

By means of lateral shifting of the lens assembly 44 the illuminating beam path and thus the axis $R_i$ thereof can be tracked to a changing focus of the main objective 20. For example, in case of a changing working distance according to FIG. 3 the transition of the angle θ from $θ_2$ to $θ_1$ is carried out by a lateral shifting, as illustrated in FIG. 3, of the lens assembly 44 towards the left, i.e. in the direction of the main objective 20. The lateral shifting in this embodiment takes place along a line of intersection of two planes, one of said planes extending parallel to the object plane 100 and the other one of said planes being spanned by the axes $R_o$ and $R_i$.

Deviating from the arrangement illustrated in FIG. 3 also slight modifications can be applied. For example, the lens assembly 44 can in a specific lateral position coincide with the optical axis thereof with the axis $R_i$ of the illuminating beam path. Further, instead of a shifting parallel to the object plane 100 also a shifting perpendicular to the axis $R_i$ of the illuminating beam path can be carried out. As already mentioned, circular arc shifts, for example along a circular arc with the center in the point of incidence of the axis $R_i$ on the deflector element 43, are also conceivable. However, here it has to be taken into account that a coupling of the focal length variation of the main objective with a linear movement of the lens assembly 44 can be realized in a technically easier way than the coupling with a rotary movement. In this connection, it is moreover pointed out once again that the deflector element 43 does not have to be tiltably mounted about an axis, as the lateral shifting of the lens assembly is alone suitable to make an illumination centering within the possible operating distances of the main objective 20 possible.

It is advantageous when a control unit 90 is provided for the coupling of a variation of the focal length of the main objective with an amount of the lateral shifting of the lens assembly 44 of the illuminating unit 40. The control unit 90 is schematically illustrated in FIG. 3, a signal being supplied to the control unit via an input thereof, which signal indicates a variation of the focal length of the main objective 20 and the respective required amount of shifting of the lens assembly 44 being output via an output of the control unit 90. The relation between the amount of shift and the variation in focal length can practically be established in a simple way with the aid of known software by the so-called "ray tracing" and a best-fit method. The lateral shifting of the illuminating axis $R_i$ on the object plane 100 hereby depends on the image scale of the lens assembly 44 and the lateral shifting of this lens assembly 44.

The possibilities of varying the focal length of a main objective 20 have already been mentioned in the introductory part of the specification. Common is the combination of a fixed and a movable lens for varying the focal length and the intercept length of the main objective. The movement of the movable lens can be measured directly and can be assigned to the varying intercept length of the main objective or its working distance. Altogether, the illumination centering according to the invention can thus be put into practice with known control methods.

LIST OF REFERENCE NUMERALS 10 microscope
20 main objective
23 optical axis
30 zoom system
40 illuminating unit
41 collector
42 diaphragm, iris diaphragm
43 illumination deflector element
44 lens assembly
50 deflector element
51 deflector element
52 deflector element
60 tube
70 eyepiece
80 light guide
90 control unit
100, 100' object plane
110 observer
I first horizontal plane
II second horizontal plane
$R_o$ viewing axis
$R_i$ illuminating axis
θ angle $R_i$ to $R_o$

The invention claimed is:

1. A microscope comprising:
a main objective having a variable focal length;
an illuminating unit comprising a light source and an illuminating optical system for generating an illuminating beam path directed onto an object plane and extending outside the main objective; and
means for centering the illumination dependent on various focal lengths of the main objective; wherein
the illuminating optical system is at least in part mounted in a laterally shiftable manner for centering the illumination;
the illuminating unit has as an illuminating optical system a collector, a diaphragm, an illumination deflector element as well as a lens assembly for focusing the illuminating beam path onto the object plane; and
the symmetrical axis of the lens assembly is aligned perpendicular to the object plane.

2. The microscope according to claim 1, wherein the illuminating optical system has a lens assembly that is at least in part mounted in a laterally shiftable manner.

3. The microscope according to claim 2, wherein the illumination deflector element has a fixed position.

4. The microscope according to claim 1, wherein the illuminating optical system has a lens assembly that is at least in part mounted in a laterally shiftable manner.

5. The microscope according to claim 1, wherein the illumination deflector element has a fixed position.

6. The microscope according to claim 1, wherein the lens assembly is at least in part shiftably mounted parallel to the object plane.

7. The microscope according to claim 1, wherein a control unit for coupling a variation of the focal length of the main objective with an amount of lateral shift of the at least one part of the illuminating optical system is provided.

8. The microscope according to claim 1, wherein the microscope comprises a zoom system arranged downstream of the main objective as viewed from the object plane.

9. The microscope according to claim 8, wherein a deflector element is arranged between the zoom system and the main objective, said deflector element directing the viewing beam path coming from the main objective into a first horizontal plane in which the longitudinal axis of the zoom system lies.

10. The microscope according to claim 9, wherein that the microscope comprises a tube and at least one eyepiece which are arranged downstream of the zoom system, and at least the tube is arranged with its longitudinal axis in a second horizontal plane which runs substantially parallel to the first horizontal plane.

11. The microscope according to claim 1, wherein the microscope comprises a tube and at least one eyepiece that are arranged downstream of the zoom system.

12. The microscope according to claim 1, wherein the microscope is designed as a stereomicroscope.

13. The microscope according to claim 12, wherein the microscope is designed as a surgical microscope.

14. A microscope comprising:
a main objective having a variable focal length;
an illuminating unit comprising a light source and an illuminating optical system for generating an illuminating beam path directed onto an object plane and extending outside the main objective; and
means for centering the illumination dependent on various focal lengths of the main objective; wherein
the illuminating optical system is at least in part mounted in a laterally shiftable manner for centering the illumination;
the illuminating unit has as an illuminating optical system a collector, a diaphragm, an illumination deflector element as well as a lens assembly for focusing the illuminating beam path onto the object plane; and
the symmetrical axis of the lens assembly is aligned parallel to the axis ($R_i$) of the illuminating beam path.

15. The microscope according to claim 14, wherein the illuminating optical system has a lens assembly that is at least in part mounted in a laterally shiftable manner.

16. The microscope according to claim 15, wherein the illumination deflector element has a fixed position.

17. The microscope according to claim 14, wherein the illuminating optical system has a lens assembly that is at least in part mounted in a laterally shiftable manner.

18. The microscope according to claim 14, wherein the illumination deflector element has a fixed position.

19. The microscope according to claim 14, wherein the lens assembly is at least in part shiftably mounted parallel to the object plane.

20. The microscope according to claim 14, wherein a control unit for coupling a variation of the focal length of the main objective with an amount of lateral shift of the at least one part of the illuminating optical system is provided.

21. The microscope according to claim 14, wherein the microscope comprises a zoom system arranged downstream of the main objective as viewed from the object plane.

22. The microscope according to claim 21, wherein a deflector element is arranged between the zoom system and the main objective, said deflector element directing the viewing beam path coming from the main objective into a first horizontal plane in which the longitudinal axis of the zoom system lies.

23. The microscope according to claim 14, wherein the microscope comprises a tube and at least one eyepiece that are arranged downstream of the zoom system.

24. The microscope according to claim 22, wherein the microscope comprises a tube and at least one eyepiece which are arranged downstream of the zoom system, and at least the tube is arranged with its longitudinal axis in a second horizontal plane which runs substantially parallel to the first horizontal plane.

25. The microscope according to claim 14, wherein the microscope is designed as a stereomicroscope.

26. The microscope according to claim 25, wherein the microscope is designed as a surgical microscope.

* * * * *